United States Patent
Chung

(10) Patent No.: US 11,333,347 B2
(45) Date of Patent: May 17, 2022

(54) ILLUMINATION DEVICE

(71) Applicant: PARAGON SEMICONDUCTOR LIGHTING TECHNOLOGY CO., LTD., New Taipei (TW)

(72) Inventor: Chia-Tin Chung, Miaoli County (TW)

(73) Assignee: PARAGON SEMICONDUCTOR LIGHTING TECHNOLOGY CO., LTD., New Taipei (TW)

( * ) Notice: Subject to any disclaimer, the term of this patent is extended or adjusted under 35 U.S.C. 154(b) by 0 days.

(21) Appl. No.: 17/145,404

(22) Filed: Jan. 11, 2021

(65) Prior Publication Data

US 2022/0090778 A1    Mar. 24, 2022

(30) Foreign Application Priority Data

Sep. 23, 2020 (TW) ................................ 109212536

(51) Int. Cl.
| | |
|---|---|
| *F21V 33/00* | (2006.01) |
| *F24F 13/078* | (2006.01) |
| *A61L 9/20* | (2006.01) |
| *F21Y 115/10* | (2016.01) |

(52) U.S. Cl.
CPC ............ *F21V 33/0088* (2013.01); *A61L 9/20* (2013.01); *F24F 13/078* (2013.01); *A61L 2209/12* (2013.01); *F21Y 2115/10* (2016.08)

(58) Field of Classification Search
CPC .... F21V 33/0088; F21V 23/0471; A61L 9/20; A61L 2209/12; A61L 2209/00; A61L 2209/111; F24F 13/078; F24F 13/06; F24F 7/003; F24F 2221/02; F21Y 2115/10

See application file for complete search history.

(56) References Cited

U.S. PATENT DOCUMENTS

| | | | | |
|---|---|---|---|---|
| 7,763,212 | B2 * | 7/2010 | McEllen | .................. A61L 9/20 422/121 |
| 8,080,203 | B2 * | 12/2011 | First | ........................ A61L 9/20 422/24 |
| 2010/0196214 | A1 * | 8/2010 | Graff | ..................... F24F 13/078 422/121 |
| 2017/0321877 | A1 * | 11/2017 | Polidoro | ............. F21V 33/0088 |

* cited by examiner

*Primary Examiner* — Bao Q Truong
(74) *Attorney, Agent, or Firm* — Li & Cai Intellectual Property Office

(57) ABSTRACT

An illumination device includes a first light-emitting module, a second light-emitting module and an airflow-guiding structure. The second light-emitting module is adjacent to the first light-emitting module. The airflow-guiding structure includes a receiving casing, a first air inlet pipe in air communication with the receiving casing, and a first air outlet pipe in air communication with the receiving casing. The first light-emitting module is received inside the airflow-guiding structure. When external air flows into the receiving casing through the first air inlet pipe by natural convection, the external air inside the receiving casing is sterilized by a sterilization light source provided by the first light-emitting module, and the external air that has been sterilized by the sterilization light source flows out of the receiving casing through the first air outlet pipe by natural convection, and is then discharged out of the illumination device.

9 Claims, 13 Drawing Sheets

ILLUMINATION DEVICE

CROSS-REFERENCE TO RELATED PATENT APPLICATION

This application claims the benefit of priority to Taiwan Patent Application No. 109212536, filed on Sep. 23, 2020. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to an illumination device, and more particularly to an illumination device with sterilization function.

BACKGROUND OF THE DISCLOSURE

In the related art, a conventional illumination device with sterilization function has been widely used, but the conventional illumination device with sterilization function still has room for improvement.

SUMMARY OF THE DISCLOSURE

In response to the above-referenced technical inadequacies, the present disclosure provides an illumination device.

In one aspect, the present disclosure provides an illumination device including a first light-emitting module, a second light-emitting module and an airflow-guiding structure. The second light-emitting module is adjacent to the first light-emitting module. The airflow-guiding structure includes a receiving casing for receiving the first light-emitting module, a first air inlet pipe in air communication with the receiving casing, and a first air outlet pipe in air communication with the receiving casing. When external air flows into the receiving casing through the first air inlet pipe by natural convection, the external air inside the receiving casing is sterilized by a sterilization light source provided by the first light-emitting module, and the external air that has been sterilized by the sterilization light source provided by the first light-emitting module flows out of the receiving casing through the first air outlet pipe by natural convection, and is then discharged out of the illumination device.

In another aspect, the present disclosure provides an illumination device including a first light-emitting module, a second light-emitting module and an airflow-guiding structure. The second light-emitting module is adjacent to the first light-emitting module. The airflow-guiding structure includes a receiving casing, a first air inlet pipe in air communication with the receiving casing, and a first air outlet pipe in air communication with the receiving casing. The first light-emitting module is received inside the airflow-guiding structure.

In yet another aspect, the present disclosure provides an illumination device including an ultraviolet-C (UV-C) radiation generating module, an illumination generating module and an airflow-guiding structure. The UV-C radiation generating module is used for providing UV-C radiation having a wavelength between 100 nm and 280 nm. The illumination generating module is adjacent to the UV-C radiation generating module. The airflow-guiding structure includes a receiving casing for receiving the UV-C radiation generating module and at least one first air outlet opening in air communication with the receiving casing. When external air flows into the receiving casing by natural convection, the external air inside the receiving casing is sterilized by the UV-C radiation provided by the UV-C radiation generating module, and the external air that has been sterilized by the UV-C radiation provided by the UV-C radiation generating module flows out of the receiving casing through the at least one first air outlet opening by natural convection, and is then discharged out of the illumination device.

Therefore, by virtue of "the airflow-guiding structure including a receiving casing and at least one first air outlet pipe in air communication with the receiving casing" and "the first light-emitting module (such as the UV-C radiation generating module) being received inside the airflow-guiding structure", when the external air flows into the receiving casing by natural convection, the external air inside the receiving casing is sterilized by the UV-C radiation provided by the UV-C radiation generating module, and the external air that has been sterilized by the UV-C radiation provided by the UV-C radiation generating module flows out of the receiving casing through the at least one first air outlet pipe by natural convection, and is then discharged out of the illumination device.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings in which.

DETAILED DESCRIPTION OF THE EXEMPLARY EMBODIMENTS

Figure 1:
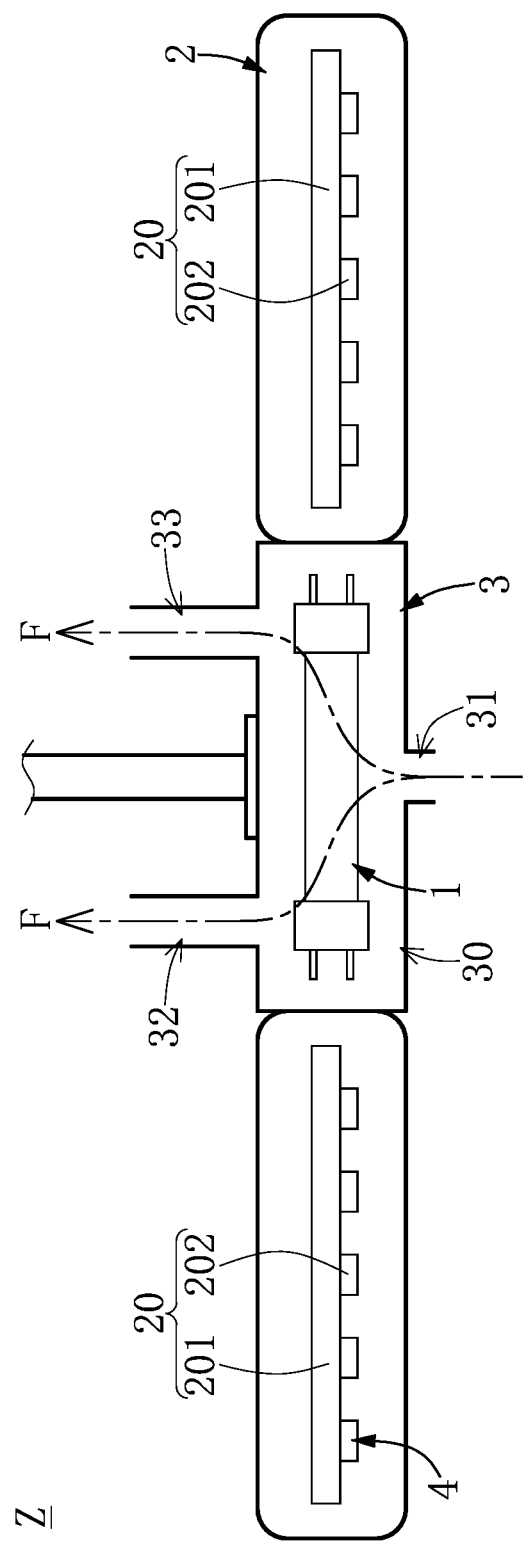
FIG. 1 is a lateral schematic view of an illumination device according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Referring to FIG. 1 to FIG. 12, the present disclosure provides an illumination device Z including a first light-emitting module 1, a second light-emitting module 2, and an airflow-guiding structure 3. The second light-emitting module 2 is adjacent to the first light-emitting module 1. The airflow-guiding structure 3 includes a receiving casing 30, a first air inlet pipe 31 in air communication with the receiving casing 30, and a first air outlet pipe 32 in air communication with the receiving casing 30, and the first light-emitting module 1 is received inside the airflow-guiding structure 3.

First Embodiment

Figure 2:
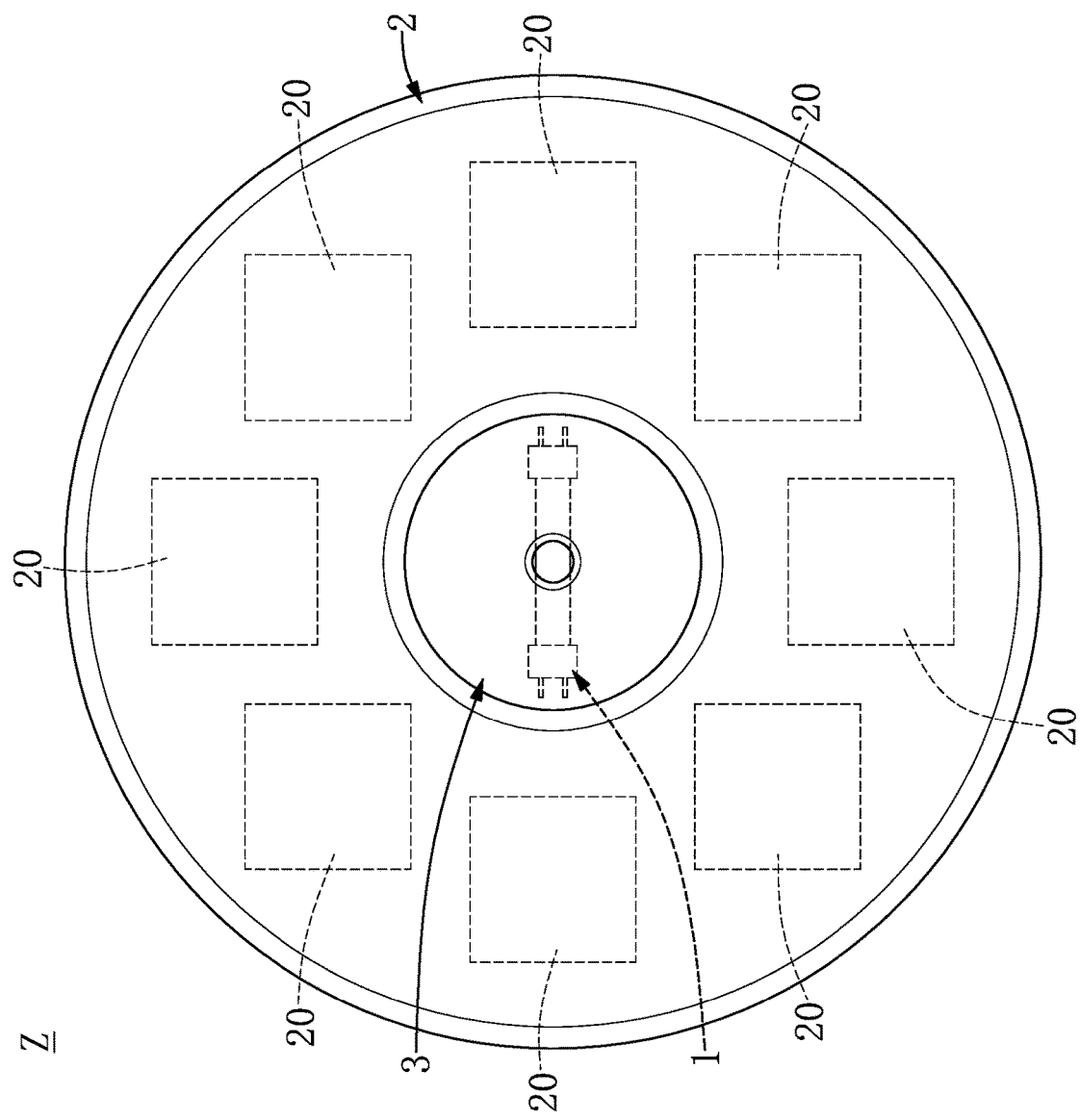
FIG. 2 is a bottom schematic bottom view of the illumination device according to the first embodiment of the present disclosure.

Referring to FIG. 1 and FIG. 2, a first embodiment of the present disclosure provides an illumination device Z including a first light-emitting module 1, a second light-emitting module 2, and an airflow-guiding structure 3. The second light-emitting module 2 is adjacent to the first light-emitting module 1. The airflow-guiding structure 3 includes a receiving casing 30 for receiving the first light-emitting module 1, a first air inlet pipe 31 (or an intake pipe) in air communication with the receiving casing 30, and a first air outlet pipe 32 (or an exhaust pipe) in air communication with the receiving casing 30. Therefore, when (or after) external air F flows into the receiving casing 30 through the first air inlet pipe 31 by natural convection, the external air F inside the receiving casing 30 can be sterilized by a sterilization light source that is provided (or generated) by the first light-emitting module 1, and the external air F that has been sterilized by the sterilization light source provided by the first light-emitting module 1 can flow out of the receiving casing 30 through the first air outlet pipe 32 by natural convection, and can then be discharged out of the illumination device Z.

More particularly, as shown in FIG. 1, the airflow-guiding structure 3 further includes a second air outlet pipe 33 in air communication with the receiving casing 30, and the external air F that has been sterilized by the sterilization light source provided by the first light-emitting module 1 can flow out of the receiving casing 30 through the second air outlet pipe 33 by natural convection, and can then be discharged out of the illumination device Z. That is to say, the external air F that has been sterilized by the sterilization light source provided by the first light-emitting module 1 can flow out of the receiving casing 30 through the first air outlet pipe 32 and the second air outlet pipe 33 by natural convection, and can then be discharged out of the illumination device Z.

For example, referring to FIG. 1 and FIG. 2, the illumination device Z of the first embodiment of the present disclosure further includes a motion detection module 4 (can be omitted), and the motion detection module 4 can be disposed on the second light-emitting module 2 or adjacent to the second light-emitting module 2. More particularly, the second light-emitting module 2 includes a plurality of illumination assemblies 20, and each illumination assembly 20 includes a circuit substrate 201 and a plurality of LED chips 202 disposed on the circuit substrate 201. In addition, the motion detection module 4 includes one or more motion sensors, and the motion detection module 4 can be disposed on the circuit substrate 201 and electrically connected to the circuit substrate 201 (as shown in FIG. 1), or the motion detection module 4 can be adjacent to the circuit substrate 201 and is not disposed on the circuit substrate 201. However, the aforementioned description is merely an example and is not meant to limit the scope of the present disclosure.

For example, referring to FIG. 1 and FIG. 2, the first light-emitting module 1 can be surrounded by the second light-emitting module 2 (as shown in FIG. 1) or juxtaposed with the second light-emitting module 2. In addition, the first light-emitting module 1 can be an ultraviolet-C (UV-C) radiation generating module (such as a UV-C lamp) for providing UV-C radiation having a wavelength substantially between 100 nm and 280 nm, and the second light-emitting module 2 can be an illumination generating module (such as an LED lamp) for generating an illumination light source. Therefore, when the external air F flows into the receiving casing 30 by natural convection, the external air F inside the receiving casing 30 can be sterilized by the UV-C radiation provided by the UV-C radiation generating module, and the external air F that has been sterilized by the UV-C radiation provided by the UV-C radiation generating module can flow out of the receiving casing 30 through the first air outlet pipe 32 and the second air outlet pipe 33 by natural convection, and can then be discharged out of the illumination device Z.

It should be noted that as shown in FIG. 1, the illumination device Z of the present disclosure can be hung from a ceiling by a supporting structure (not labeled). However, the aforementioned description is merely an example and is not meant to limit the scope of the present disclosure.

Second Embodiment

Figure 3:
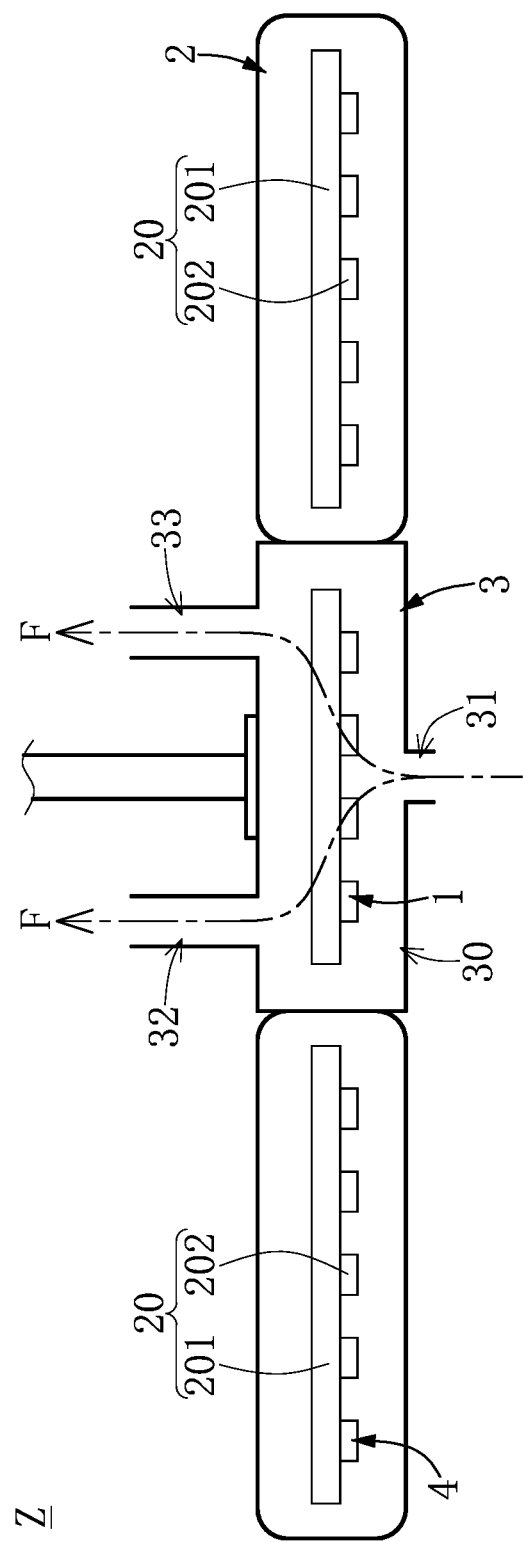
FIG. 3 is a lateral schematic view of an illumination device according to a second embodiment of the present disclosure.

Referring to FIG. 3, a second embodiment of the present disclosure provides an illumination device Z including a first light-emitting module 1, a second light-emitting module 2, and an airflow-guiding structure 3. Comparing FIG. 3 with FIG. 1, the difference between the second embodiment and the first embodiment is as follows: in the second embodiment, the first light-emitting module 1 can be a UV-C LED module for providing UV-C radiation having a wavelength substantially between 100 nm and 280 nm, and the UV-C LED module includes a plurality of UV-C LED chips. In other words, according to different requirements, the UV-C lamp in the first embodiment can be replaced with the UV-C LED chips.

Third Embodiment

Figure 4:
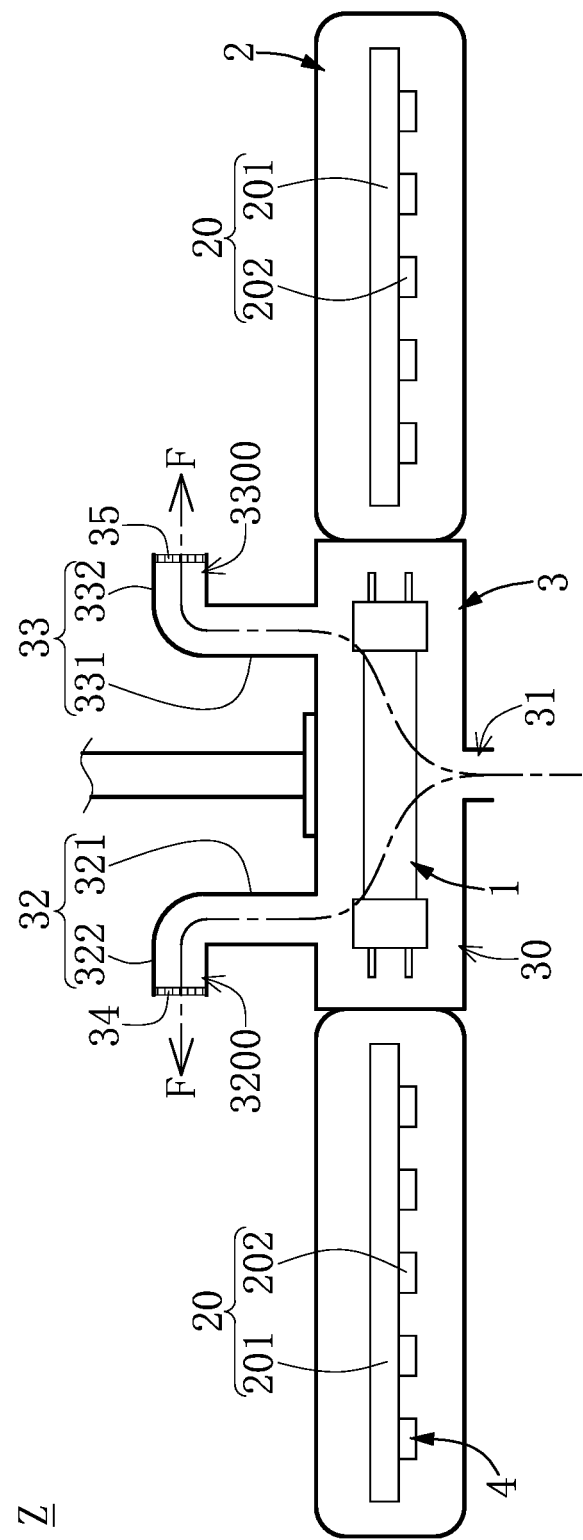
FIG. 4 is a lateral schematic view of an illumination device according to a third embodiment of the present disclosure.

Referring to FIG. 4, a third embodiment of the present disclosure provides an illumination device Z including a first light-emitting module 1, a second light-emitting module 2, and an airflow-guiding structure 3. Comparing FIG. 4 with FIG. 1, the difference between the third embodiment and the first embodiment is as follows: in the third embodiment, the first air outlet pipe 32 includes a first vertical air outlet portion 321 in air communication with the receiving casing 30 and a first horizontal air outlet portion 322 in air communication with the first vertical air outlet portion 321, and the second air outlet pipe 33 includes a second vertical air outlet portion 331 in air communication with the receiving casing 30 and a second horizontal air outlet portion 332 in air communication with the second vertical air outlet portion 331. It should be noted that the first air outlet pipe 32 includes a first air outlet opening 3200, and the airflow-guiding structure 3 includes a first air outlet filter 34 disposed inside the first air outlet opening 3200. In addition, the second air outlet pipe 33 includes a second air outlet opening 3300, and the airflow-guiding structure 3 includes a second air outlet filter 35 disposed inside the second air outlet opening 3300.

Therefore, by virtue of the first horizontal air outlet portion 322 and the second horizontal air outlet portion 332, foreign matter in the external environment cannot fall into the first air outlet pipe 32 and the second air outlet pipe 33 from a position above the first air outlet pipe 32 and the second air outlet pipe 33. In addition, the first air outlet filter 34 and the second air outlet filter 35 can be used to effectively prevent the foreign matter in the external environment from entering into the first air outlet pipe 32 and the second air outlet pipe 33.

Fourth Embodiment

Figure 5:
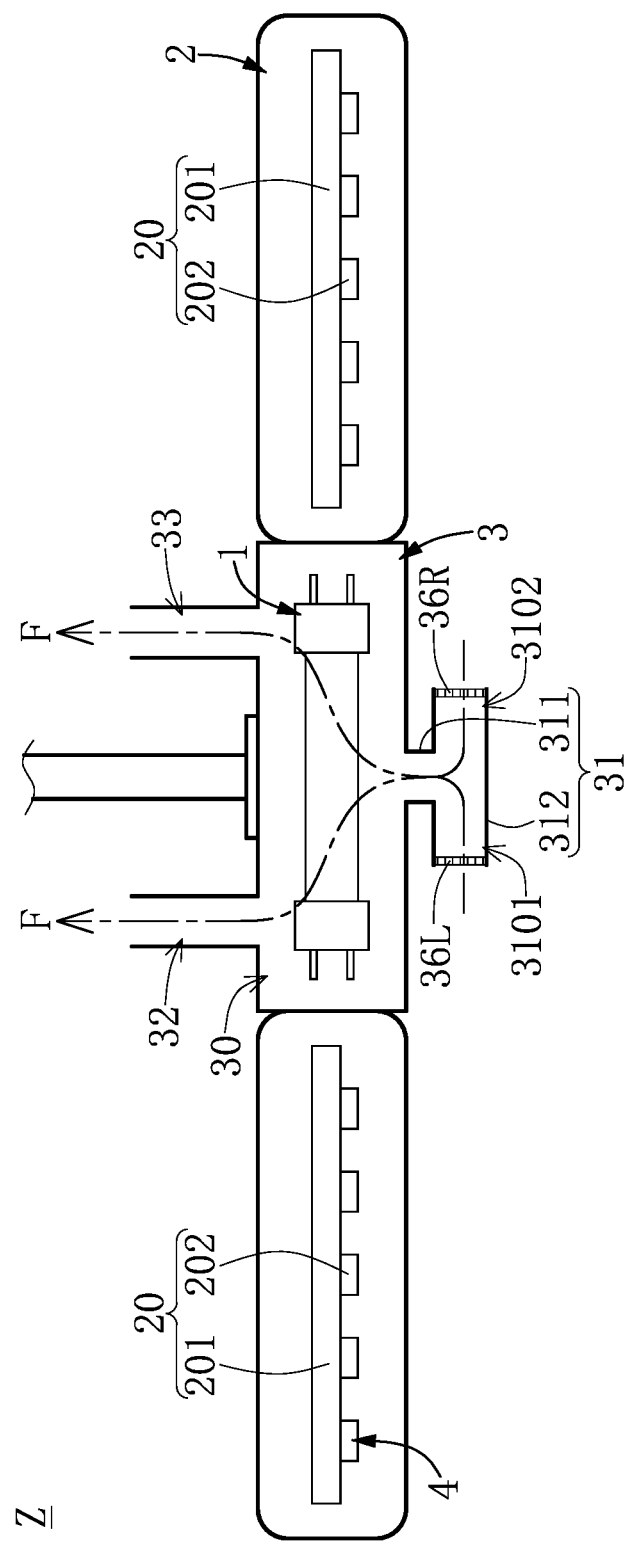
FIG. 5 is a lateral schematic view of an illumination device according to a fourth embodiment of the present disclosure.

Referring to FIG. 5, a fourth embodiment of the present disclosure provides an illumination device Z including a first light-emitting module 1, a second light-emitting module 2, and an airflow-guiding structure 3. Comparing FIG. 5 with FIG. 1, the difference between the fourth embodiment and the first embodiment is as follows: in the fourth embodiment, the first air inlet pipe 31 includes a first left air inlet opening 3101 and a first right air inlet opening 3102, and the airflow-guiding structure 3 includes a first left filter 36L disposed inside the first left air inlet opening 3101 and a first right filter 36R disposed inside the first right air inlet opening 3102. In addition, the first air inlet pipe 31 includes a first vertical air inlet portion 311 in air communication with the receiving casing 30 and a first horizontal air inlet portion 312 in air communication with the first vertical air inlet portion 311, and the first left air inlet opening 3101 and the first right air inlet opening 3102 are respectively formed on two opposite lateral sides of the first horizontal air inlet portion 312. Therefore, the first left filter 36L and the first right filter 36R can be used to effectively prevent the foreign matter in the external environment from entering into the first air inlet pipe 31.

It should be noted that the first air inlet pipe 31 is disposed on a bottom side of the airflow-guiding structure 3, so that the sterilization light source provided by the first light-emitting module 1 can be blocked by the first horizontal air inlet portion 312 of the first air inlet pipe 31 so as to prevent the sterilization light source provided by the first light-emitting module 1 from being projected onto a region under the first air inlet pipe 31.

Fifth Embodiment

Figure 6:
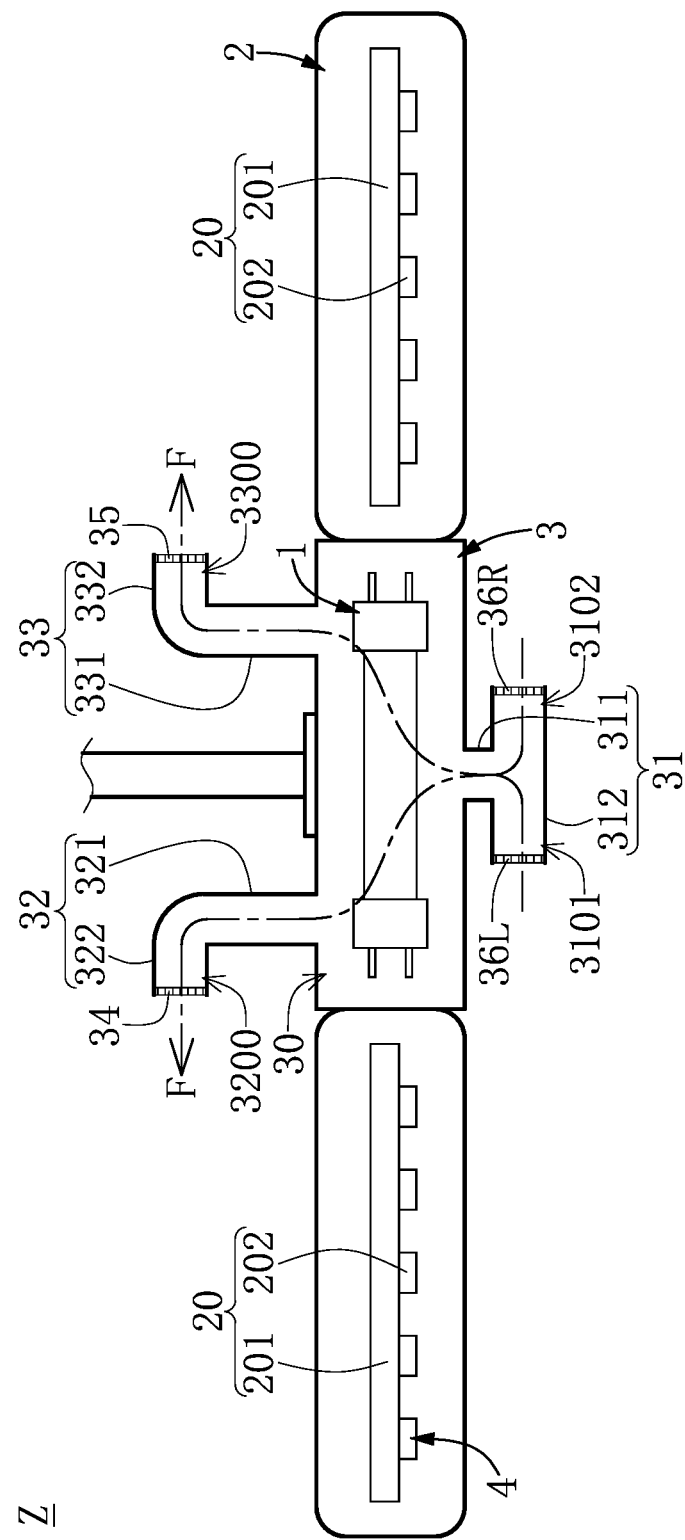
FIG. 6 is a lateral schematic view of an illumination device according to a fifth embodiment of the present disclosure.

Referring to FIG. 6, a fifth embodiment of the present disclosure provides an illumination device Z including a first light-emitting module 1, a second light-emitting module 2, and an airflow-guiding structure 3. Comparing FIG. 6 with FIG. 1, the difference between the fifth embodiment and the first embodiment is as follows: in the fifth embodiment, the first air outlet pipe 32 includes a first vertical air outlet portion 321 in air communication with the receiving casing 30 and a first horizontal air outlet portion 322 in air communication with the first vertical air outlet portion 321, and the second air outlet pipe 33 includes a second vertical air outlet portion 331 in air communication with the receiving casing 30 and a second horizontal air outlet portion 332 in air communication with the second vertical air outlet portion 331. It should be noted that the first air outlet pipe 32 includes a first air outlet opening 3200, and the airflow-guiding structure 3 includes a first air outlet filter 34 disposed inside the first air outlet opening 3200. In addition, the second air outlet pipe 33 includes a second air outlet opening 3300, and the airflow-guiding structure 3 includes a second air outlet filter 35 disposed inside the second air outlet opening 3300. Therefore, by virtue of the first horizontal air outlet portion 322 and the second horizontal air outlet portion 332, foreign matter in the external environment cannot fall into the first air outlet pipe 32 and the second air outlet pipe 33 from a position above the first air outlet pipe 32 and the second air outlet pipe 33. In addition, the first air outlet filter 34 and the second air outlet filter 35 can be used to effectively prevent the foreign matter in the external environment from entering into the first air outlet pipe 32 and the second air outlet pipe 33.

According to the above description, the first air inlet pipe 31 includes a first left air inlet opening 3101 and a first right air inlet opening 3102, and the airflow-guiding structure 3 includes a first left filter 36L disposed inside the first left air inlet opening 3101 and a first right filter 36R disposed inside the first right air inlet opening 3102. In addition, the first air inlet pipe 31 includes a first vertical air inlet portion 311 in air communication with the receiving casing 30 and a first horizontal air inlet portion 312 in air communication with the first vertical air inlet portion 311, and the first left air inlet opening 3101 and the first right air inlet opening 3102 are respectively formed on two opposite lateral sides of the first horizontal air inlet portion 312. It should be noted that the first air inlet pipe 31 is disposed on a bottom side of the airflow-guiding structure 3, so that the sterilization light source provided by the first light-emitting module 1 can be blocked by the first horizontal air inlet portion 312 of the first air inlet pipe 31, so as to prevent the sterilization light source provided by the first light-emitting module 1 from being projected onto a region under the first air inlet pipe 31.

Sixth Embodiment

Figure 7:
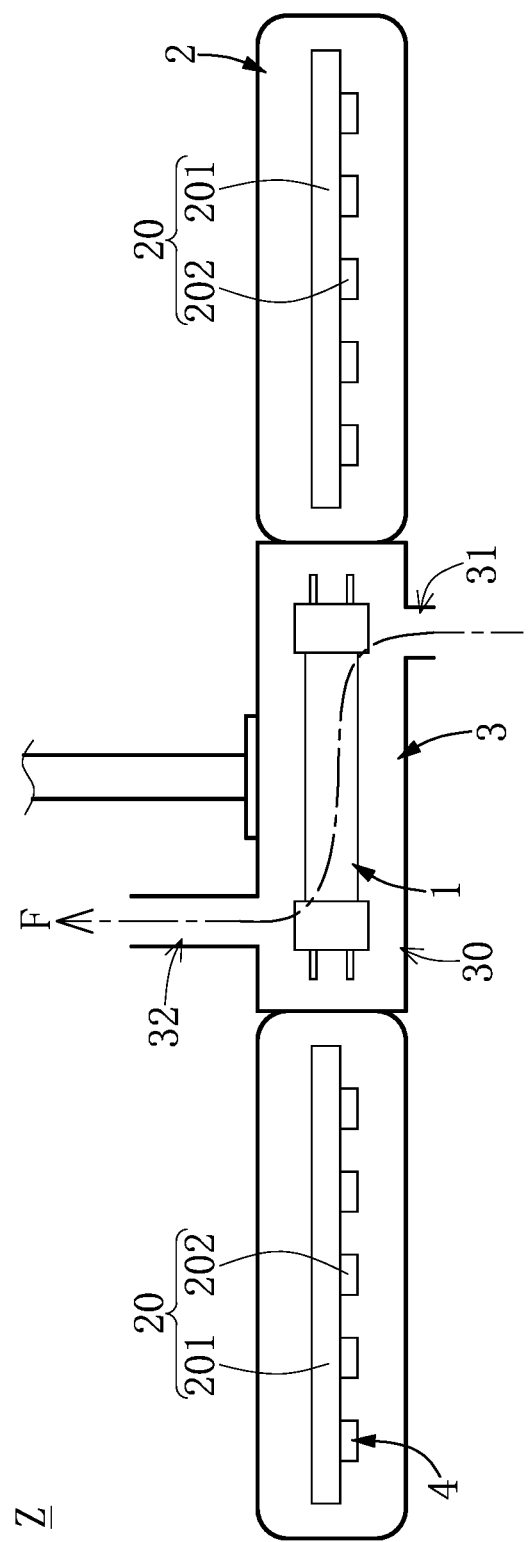
FIG. 7 is a lateral schematic view of an illumination device according to a sixth embodiment of the present disclosure.

Referring to FIG. 7, a sixth embodiment of the present disclosure provides an illumination device Z including a first light-emitting module 1, a second light-emitting module 2, and an airflow-guiding structure 3. Comparing FIG. 7 with FIG. 1, the difference between the sixth embodiment and the first embodiment is as follows: in the sixth embodiment, there is only one first air inlet pipe 31 that is in air communication with the receiving casing 30, and there is only one first air outlet pipe 32 that is in air communication with the receiving casing 30. Therefore, when external air F flows into the receiving casing 30 through the first air inlet pipe 31 by natural convection, the external air F inside the receiving casing 30 can be sterilized by the sterilization light source provided by the first light-emitting module 1, and the external air F that has been sterilized by the sterilization light source provided by the first light-emitting module 1 can flow out of the receiving casing 30 through the first air outlet pipe 32 by natural convection, and can then be discharged out of the illumination device Z. It should be noted that the longer a horizontal distance between the first inlet pipe 31 and the first outlet pipe 32 is, the more time it takes for the external air F inside the receiving casing 30 to be sterilized by the sterilization light source provided by the first light-emitting module 1.

Seventh Embodiment

Figure 8:
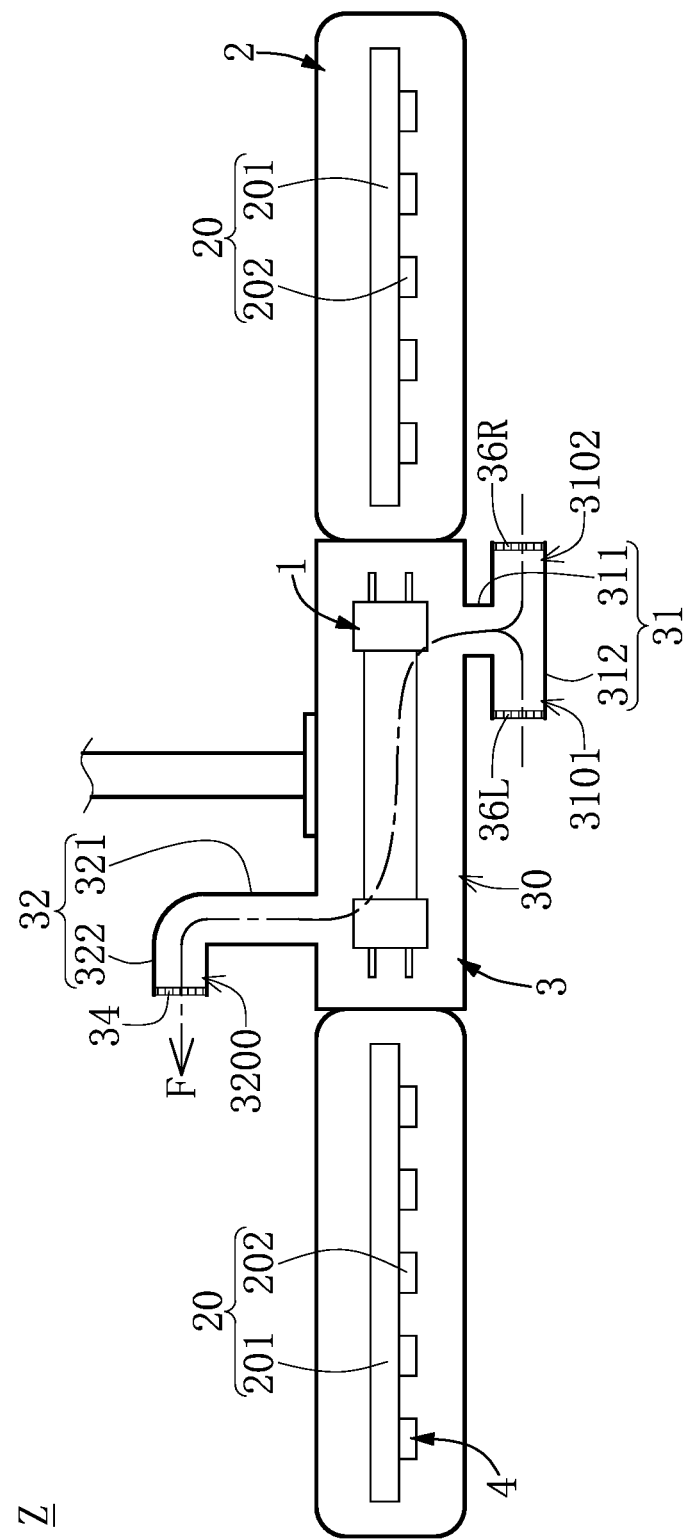
FIG. 8 is a lateral schematic view of an illumination device according to a seventh embodiment of the present disclosure.

Referring to FIG. 8, a seventh embodiment of the present disclosure provides an illumination device Z including a first light-emitting module 1, a second light-emitting module 2, and an airflow-guiding structure 3. Comparing FIG. 8 with FIG. 7, the difference between the seventh embodiment and the sixth first embodiment is as follows: in the seventh embodiment, the first air inlet pipe 31 includes a first left air inlet opening 3101 and a first right air inlet opening 3102, and the airflow-guiding structure 3 includes a first left filter 36L disposed inside the first left air inlet opening 3101 and a first right filter 36R disposed inside the first right air inlet opening 3102. In addition, the first air inlet pipe 31 includes a first vertical air inlet portion 311 in air communication with the receiving casing 30 and a first horizontal air inlet portion 312 in air communication with the first vertical air inlet portion 311, and the first left air inlet opening 3101 and the first right air inlet opening 3102 are respectively formed on two opposite lateral sides of the first horizontal air inlet portion 312. Therefore, the first left filter 36L and the first right filter 36R can be used to effectively prevent the foreign matter in the external environment from entering into the first air inlet pipe 31.

According to the above description, the first air outlet pipe 32 includes a first vertical air outlet portion 321 in air communication with the receiving casing 30 and a first horizontal air outlet portion 322 in air communication with the first vertical air outlet portion 321. In addition, the first air outlet pipe 32 includes a first air outlet opening 3200, and the airflow-guiding structure 3 includes a first air outlet filter 34 disposed inside the first air outlet opening 3200. Therefore, by virtue of the first horizontal air outlet portion 322, foreign matter in the external environment cannot fall into the first air outlet pipe 32 from a position above the first air outlet pipe 32. In addition, the first air outlet filter 34 can be used to effectively prevent the foreign matter in the external environment from entering into the first air outlet pipe 32.

It should be noted that the first air inlet pipe 31 is disposed on a bottom side of the airflow-guiding structure 3, so that the sterilization light source provided by the first light-emitting module 1 can be blocked by the first horizontal air inlet portion 312 of the first air inlet pipe 31, so as to prevent the sterilization light source provided by the first light-emitting module 1 from being projected onto a region under the first air inlet pipe 31.

Eighth Embodiment

Figure 9:
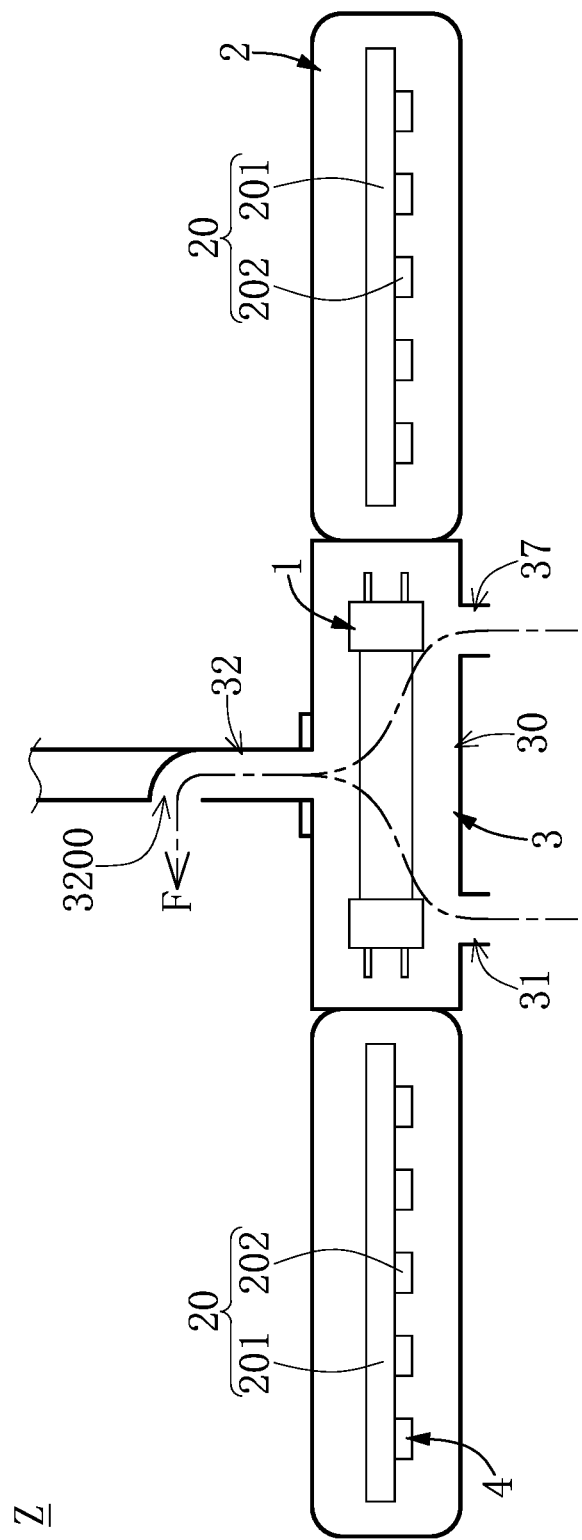
FIG. 9 is a lateral schematic view of an illumination device according to an eighth embodiment of the present disclosure.

Referring to FIG. 9, an eighth embodiment of the present disclosure provides an illumination device Z including a first light-emitting module 1, a second light-emitting module 2, and an airflow-guiding structure 3. The second light-emitting module 2 is adjacent to the first light-emitting module 1. The airflow-guiding structure 3 includes a receiving casing 30 for receiving the first light-emitting module 1, a first air inlet pipe 31 (or an intake pipe) in air communication with the receiving casing 30, and a first air outlet pipe 32 (or an exhaust pipe) in air communication with the receiving casing 30. Therefore, when (or after) external air F flows into the receiving casing 30 through the first air inlet pipe 31 by natural convection, the external air F inside the receiving casing 30 can be sterilized by a sterilization light source that is provided (or generated) by the first light-emitting module 1, and the external air F that has been sterilized by the sterilization light source provided by the first light-emitting module 1 can flow out of the receiving casing 30 through a first air outlet opening 3200 of the first air outlet pipe 32 by natural convection, and can then be discharged out of the illumination device Z.

More particularly, as shown in FIG. 9, the airflow-guiding structure 3 further includes a second air inlet pipe 37 in air communication with the receiving casing 30, and the external air F can flow into the receiving casing 30 through the second air inlet pipe 37 by natural convection. That is to say, the external air F can concurrently flow into the receiving casing 30 through the first air inlet pipe 31 and the second air inlet pipe 37 by natural convection. Therefore, when the external air F concurrently flows into the receiving casing 30 through the first air inlet pipe 31 and the second air inlet pipe 37 by natural convection, the external air F inside the receiving casing 30 can be sterilized by a sterilization light source that is provided (or generated) by the first light-emitting module 1, and the external air F that has been sterilized by the sterilization light source provided by the first light-emitting module 1 can flow out of the receiving casing 30 through the first air outlet opening 3200 of the first air outlet pipe 32 by natural convection, and can then be discharged out of the illumination device Z.

For example, referring to FIG. 9, the illumination device Z of the eighth embodiment of the present disclosure further includes a motion detection module 4 (can be omitted), and the motion detection module 4 can be disposed on the second light-emitting module 2 or adjacent to the second light-emitting module 2. More particularly, the second light-emitting module 2 includes a plurality of illumination assemblies 20, and each illumination assembly 20 includes a circuit substrate 201 and a plurality of LED chips 202 disposed on the circuit substrate 201. In addition, the motion detection module 4 includes one or more motion sensors, and the motion detection module 4 can be disposed on the circuit substrate 201 and electrically connected to the circuit substrate 201 (as shown in FIG. 9), or the motion detection module 4 can be adjacent to the circuit substrate 201 and is not disposed on the circuit substrate 201. However, the aforementioned description is merely an example and is not meant to limit the scope of the present disclosure.

For example, referring to FIG. 9, the first light-emitting module 1 can be surrounded by the second light-emitting module 2 or juxtaposed with the second light-emitting module 2. In addition, the first light-emitting module 1 can be an ultraviolet-C (UV-C) radiation generating module (such as a UV-C lamp) for providing UV-C radiation having a wavelength substantially between 100 nm and 280 nm, and the second light-emitting module 2 can be an illumination generating module (such as an LED lamp) for generating an illumination light source. Therefore, when the external air F flows into the receiving casing 30 by natural convection, the external air F inside the receiving casing 30 can be sterilized by the UV-C radiation provided by the UV-C radiation generating module, and the external air F that has been sterilized by the UV-C radiation provided by the UV-C radiation generating module can flow out of the receiving casing 30 through the first air outlet pipe 32 by natural convection, and can then be discharged out of the illumination device Z. It should be noted that as shown in FIG. 9, the illumination device Z of the present disclosure can be hung from a ceiling by the first air outlet pipe 32. However, the aforementioned description is merely an example and is not meant to limit the scope of the present disclosure.

Ninth Embodiment

Figure 10:
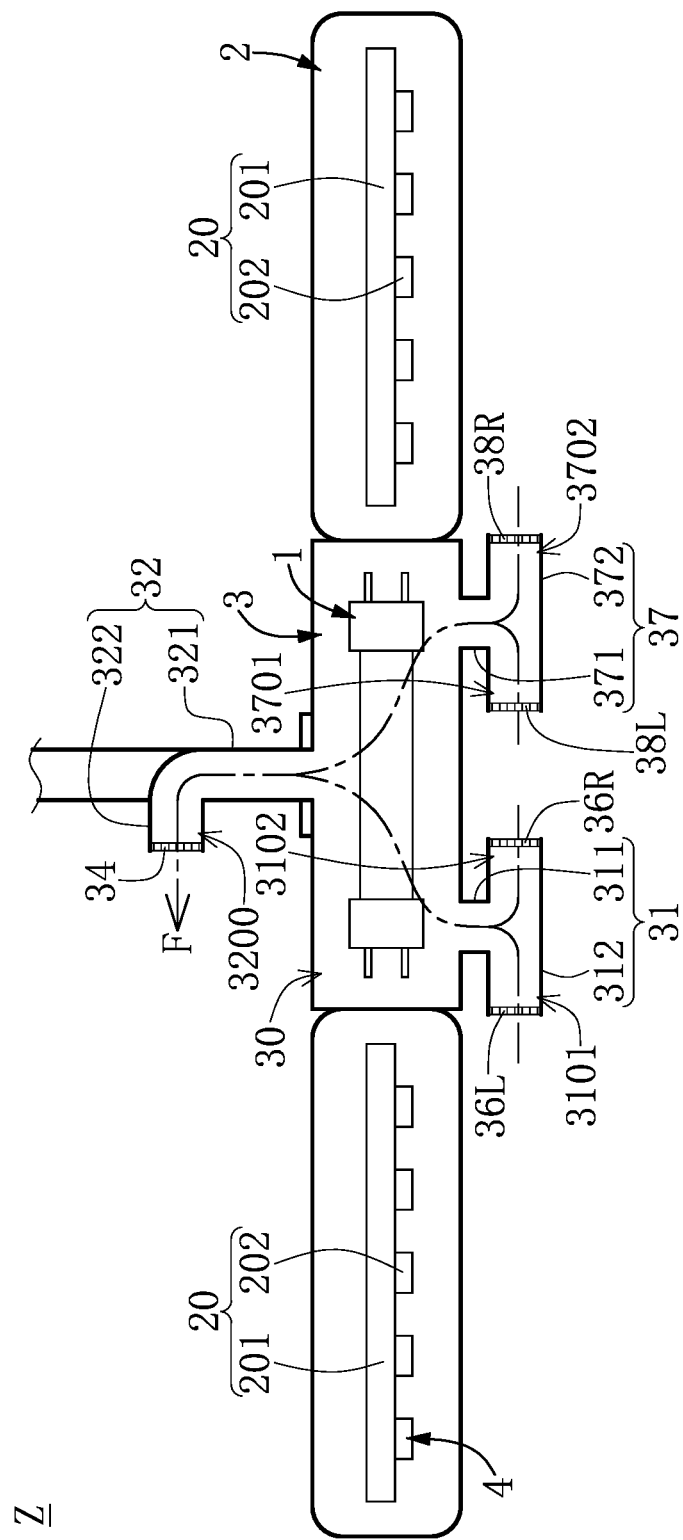
FIG. 10 is a lateral schematic view of an illumination device according to a ninth embodiment of the present disclosure.

Referring to FIG. 10, a ninth embodiment of the present disclosure provides an illumination device Z including a first light-emitting module 1, a second light-emitting module 2, and an airflow-guiding structure 3. Comparing FIG. 10 with FIG. 9, the difference between the ninth embodiment and the eighth embodiment is as follows: in the ninth embodiment, the first air inlet pipe 31 includes a first left air inlet opening 3101 and a first right air inlet opening 3102, and the airflow-guiding structure 3 includes a first left filter 36L disposed inside the first left air inlet opening 3101 and a first right filter 36R disposed inside the first right air inlet opening 3102. In addition, the first air inlet pipe 31 includes a first vertical air inlet portion 311 in air communication with the receiving casing 30 and a first horizontal air inlet portion 312 in air communication with the first vertical air inlet portion 311, and the first left air inlet opening 3101 and the first right air inlet opening 3102 are respectively formed on two opposite lateral sides of the first horizontal air inlet portion 312. Therefore, the first left filter 36L and the first right filter 36R can be used to effectively prevent the foreign matter in the external environment from entering into the first air inlet pipe 31.

According to the above description, the second air inlet pipe 37 has a second left air inlet opening 3701 and a second right air inlet opening 3702, and the airflow-guiding structure 3 includes a second left filter 38L disposed inside the second left air inlet opening 3701 and a second right filter 38R disposed inside the second right air inlet opening 3702. In addition, the second air inlet pipe 37 includes a second vertical air inlet portion 371 in air communication with the receiving casing 30 and a second horizontal air inlet portion 372 in air communication with the second vertical air inlet portion 371, and the second left air inlet opening 3701 and the second right air inlet opening 3702 are respectively formed on two opposite lateral sides of the second horizontal air inlet portion 372. Therefore, the second left filter 38L and the second right filter 38R can be used to effectively prevent the foreign matter in the external environment from entering into the second air inlet pipe 37.

According to the above description, the first air outlet pipe 32 includes a first vertical air outlet portion 321 in air communication with the receiving casing 30 and a first horizontal air outlet portion 322 in air communication with the first vertical air outlet portion 321. In addition, the first air outlet pipe 32 includes a first air outlet opening 3200, and the airflow-guiding structure 3 includes a first air outlet filter 34 disposed inside the first air outlet opening 3200. Therefore, the first air outlet filter 34 can be used to effectively prevent the foreign matter in the external environment from entering into the first air outlet pipe 32.

It should be noted that the first air inlet pipe 31 is disposed on a bottom side of the airflow-guiding structure 3, so that the sterilization light source provided by the first light-emitting module 1 can be blocked by the first horizontal air inlet portion 312 of the first air inlet pipe 31, so as to prevent the sterilization light source provided by the first light-emitting module 1 from being projected onto a region under the first air inlet pipe 31. Moreover, the second air inlet pipe 37 is disposed on a bottom side of the airflow-guiding structure 3, and a sterilization light source provided by the second light-emitting module 2 can be blocked by the second horizontal air inlet portion 372 of the second air inlet pipe 37, so as to prevent the sterilization light source provided by the second light-emitting module 2 from being projected onto a region under the second air inlet pipe 37.

Tenth Embodiment

Figure 11:
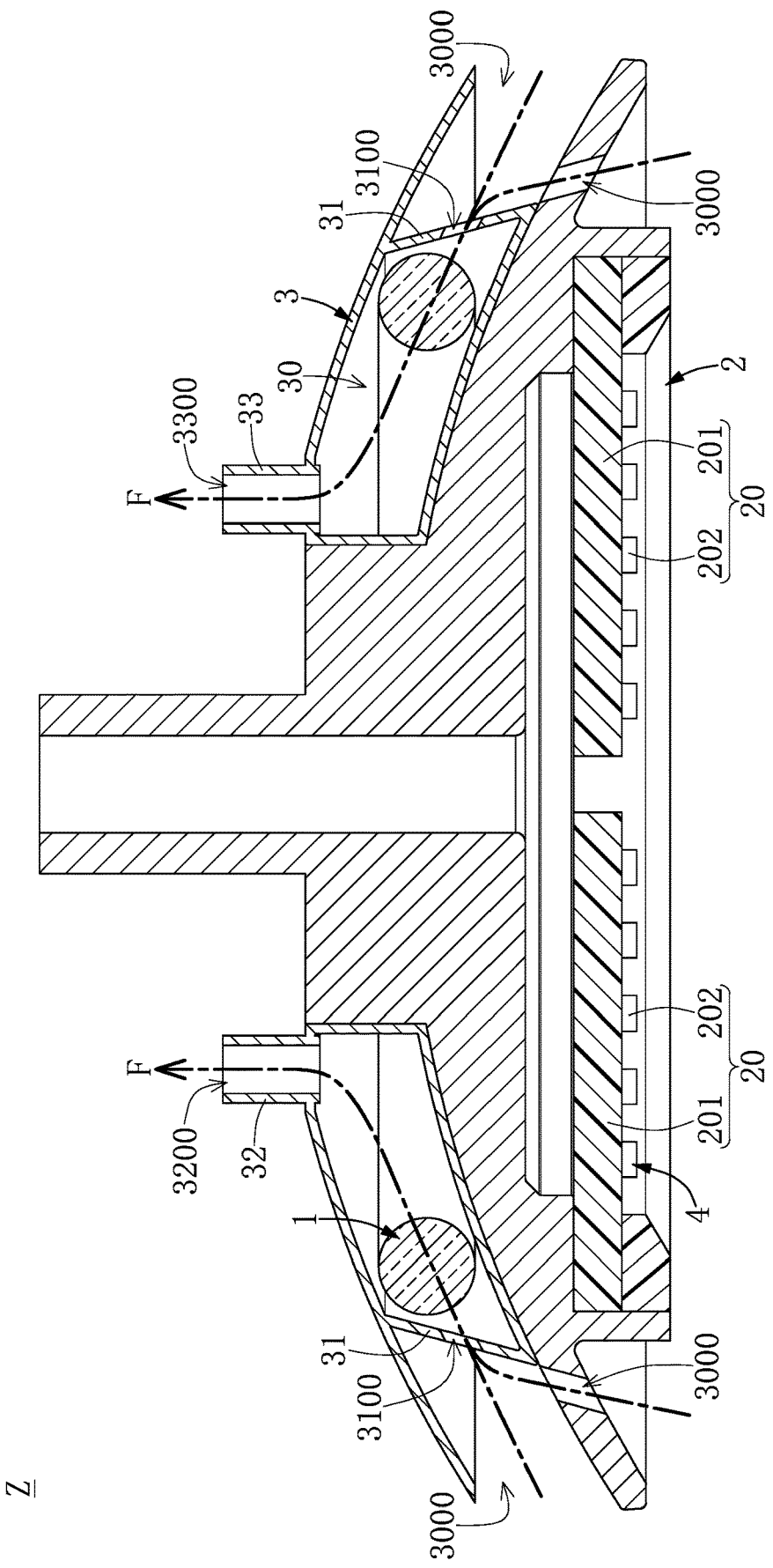
FIG. 11 is a lateral schematic view of an illumination device according to a tenth embodiment of the present disclosure.

Referring to FIG. 11, a tenth embodiment of the present disclosure provides an illumination device Z including a first light-emitting module 1, a second light-emitting module 2, and an airflow-guiding structure 3. The second light-emitting module 2 is adjacent to the first light-emitting module 1. The airflow-guiding structure 3 includes a receiving casing 30 for receiving the first light-emitting module 1, a plurality of first air inlet pipes 31 (or an intake pipe) in air communication with the receiving casing 30, and at least one first air outlet pipe 32 (or an exhaust pipe) in air communication with the receiving casing 30. Therefore, when (or after) external air F flows into the receiving casing 30 through the first air inlet pipes 31 (such as a plurality of first air inlet openings 3100) by natural convection, the external air F inside the receiving casing 30 can be sterilized by a sterilization light source that is provided (or generated) by the first light-emitting module 1, and the external air F that has been sterilized by the sterilization light source provided by the first light-emitting module 1 can flow out of the receiving casing 30 through the first air outlet pipe 32 (such as a first air outlet opening 3200) by natural convection, and can then be discharged out of the illumination device Z. It should be noted that the external air F can also flow into the first air inlet openings 3100 through a plurality of different auxiliary air inlet openings 3000 by natural convection.

More particularly, as shown in FIG. 11, the airflow-guiding structure 3 further includes a second air outlet pipe 33 in air communication with the receiving casing 30, and the external air F that has been sterilized by the sterilization light source provided by the first light-emitting module 1 can flow out of the receiving casing 30 through the second air outlet pipe 33 (such as a second air outlet opening 3300) by natural convection, and can then be discharged out of the illumination device Z. That is to say, the external air F that has been sterilized by the sterilization light source provided by the first light-emitting module 1 can flow out of the receiving casing 30 through the first air outlet pipe 32 and the second air outlet pipe 33 by natural convection, and can then be discharged out of the illumination device Z.

For example, referring to FIG. 11, the illumination device Z of the tenth embodiment of the present disclosure further includes a motion detection module 4 (can be omitted), and the motion detection module 4 can be disposed on the second light-emitting module 2 or adjacent to the second light-emitting module 2. More particularly, the second light-emitting module 2 includes a plurality of illumination assemblies 20, and each illumination assembly 20 includes a circuit substrate 201 and a plurality of LED chips 202 disposed on the circuit substrate 201. In addition, the motion detection module 4 includes one or more motion sensors, and the motion detection module 4 can be disposed on the circuit substrate 201 and electrically connected to the circuit substrate 201, or the motion detection module 4 can be adjacent to the circuit substrate 201 and is not disposed on the circuit substrate 201. However, the aforementioned description is merely an example and is not meant to limit the scope of the present disclosure.

For example, referring to FIG. 11, the first light-emitting module 1 can be an ultraviolet-C (UV-C) radiation generating module (such as a UV-C lamp) for providing UV-C radiation having a wavelength substantially between 100 nm and 280 nm, and the second light-emitting module 2 can be an illumination generating module (such as an LED lamp) for generating an illumination light source. Therefore, when the external air F flows into the receiving casing 30 by natural convection, the external air F inside the receiving casing 30 can be sterilized by the UV-C radiation provided by the UV-C radiation generating module, and the external air F that has been sterilized by the UV-C radiation provided by the UV-C radiation generating module can flow out of the receiving casing 30 through the first air outlet pipe 32 and the second air outlet pipe 33 by natural convection, and can then be discharged out of the illumination device Z. It should be noted that as shown in FIG. 11, the illumination device Z of the present disclosure can be hung from a ceiling by a supporting structure (not labeled). However, the aforementioned description is merely an example and is not meant to limit the scope of the present disclosure.

Eleventh Embodiment

Figure 12:
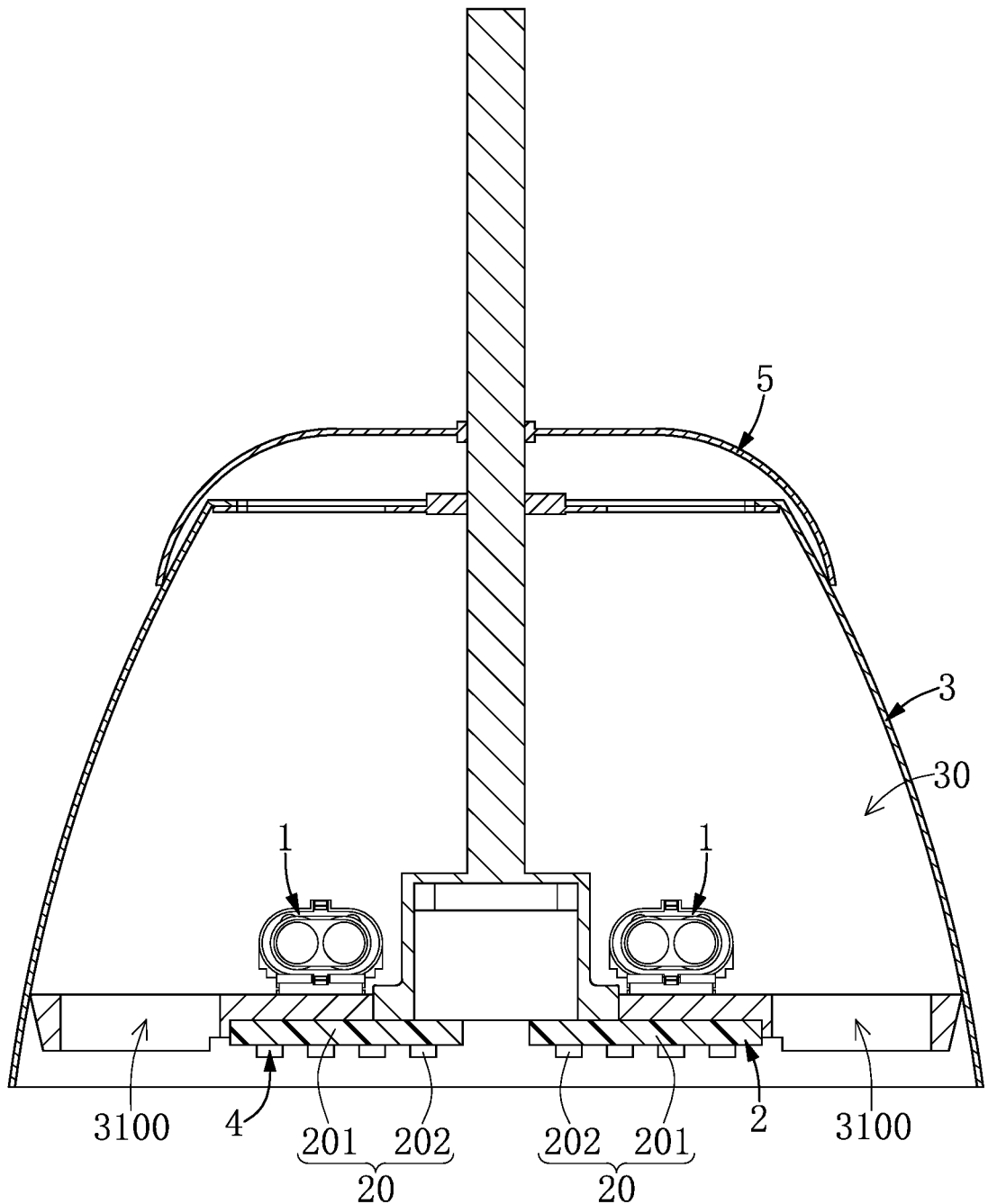
FIG. 12 is a lateral schematic view of an illumination device according to an eleventh embodiment of the present disclosure.
Figure 13:
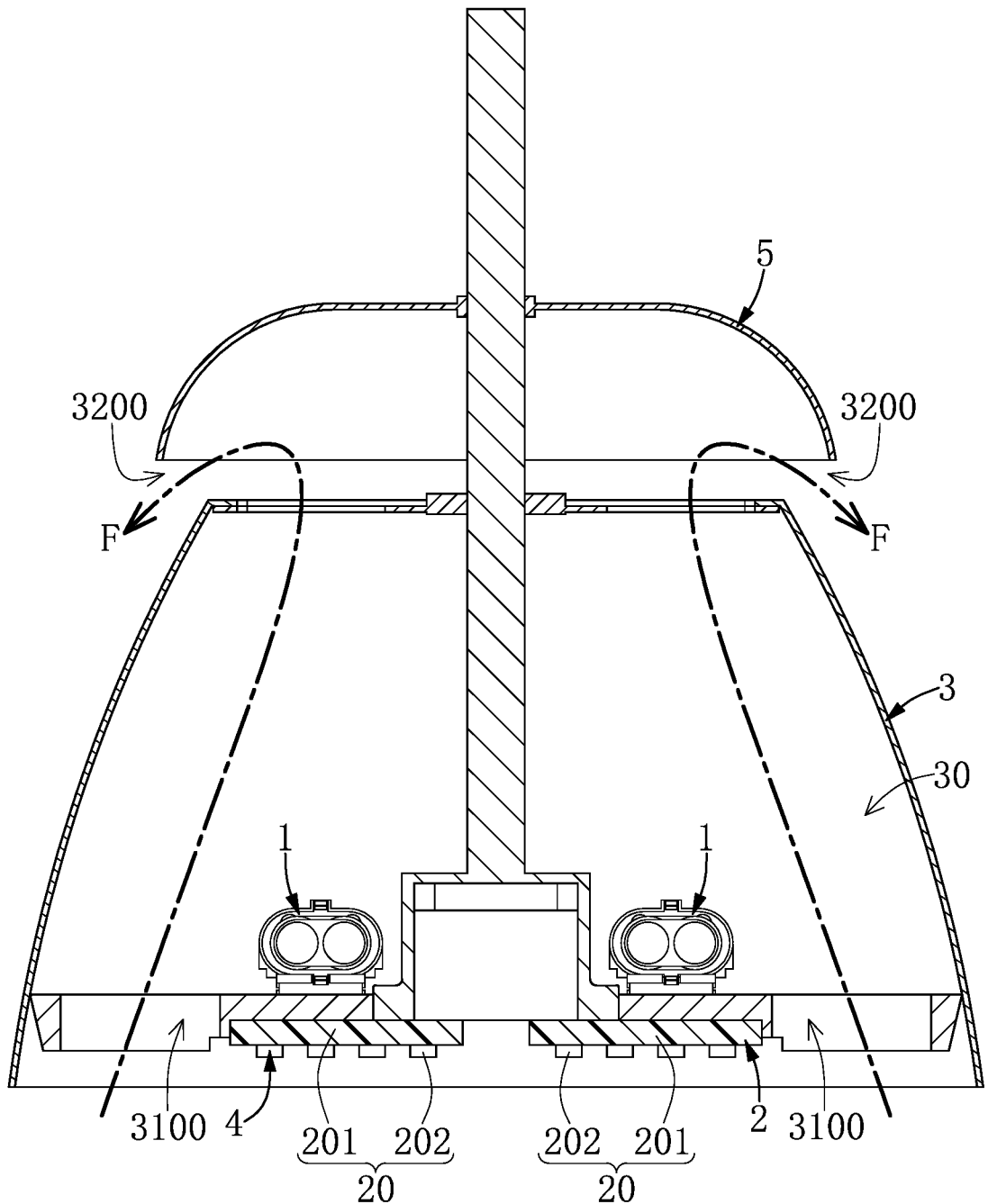
FIG. 13 is another lateral schematic view of the illumination device according to the eleventh embodiment of the present disclosure.

Referring to FIG. 12 and FIG. 13, an eleventh embodiment of the present disclosure provides an illumination device Z including a first light-emitting module 1, a second light-emitting module 2, and an airflow-guiding structure 3. The second light-emitting module 2 is adjacent to the first light-emitting module 1. The airflow-guiding structure 3 includes a receiving casing 30 for receiving the first light-emitting module 1, a plurality of first air inlet openings 3100 in air communication with the receiving casing 30, and at least one first air outlet opening 3200 in air communication with the receiving casing 30. Therefore, when (or after) external air F flows into the receiving casing 30 through the first air inlet openings 3100 by natural convection, the external air F inside the receiving casing 30 can be sterilized by a sterilization light source that is provided (or generated) by the first light-emitting module 1, and the external air F that has been sterilized by the sterilization light source provided by the first light-emitting module 1 can flow out of the receiving casing 30 through the first air outlet opening 3200 by natural convection, and can then be discharged out of the illumination device Z.

For example, referring to FIG. 12 and FIG. 13, the illumination device Z of the eleventh embodiment of the present disclosure further includes a motion detection module 4 (can be omitted), and the motion detection module 4 can be disposed on the second light-emitting module 2 or adjacent to the second light-emitting module 2. More particularly, the second light-emitting module 2 includes a plurality of illumination assemblies 20, and each illumination assembly 20 includes a circuit substrate 201 and a plurality of LED chips 202 disposed on the circuit substrate 201. In addition, the motion detection module 4 includes one or more motion sensors, and the motion detection module 4 can be disposed on the circuit substrate 201 and electrically connected to the circuit substrate 201, or the motion detection module 4 can be adjacent to the circuit substrate 201 and is not disposed on the circuit substrate 201. However, the aforementioned description is merely an example and is not meant to limit the scope of the present disclosure.

For example, referring to FIG. 12 and FIG. 13, the first light-emitting module 1 can be an ultraviolet-C (UV-C) radiation generating module (such as a UV-C lamp) for providing UV-C radiation having a wavelength substantially between 100 nm and 280 nm, and the second light-emitting module 2 can be an illumination generating module (such as an LED lamp) for generating an illumination light source. Therefore, when the external air F flows into the receiving casing 30 by natural convection, the external air F inside the receiving casing 30 can be sterilized by the UV-C radiation provided by the UV-C radiation generating module, and the external air F that has been sterilized by the UV-C radiation provided by the UV-C radiation generating module can flow out of the receiving casing 30 through the first air outlet opening 3200 by natural convection, and can then be discharged out of the illumination device Z. It should be noted that the illumination device Z of the eleventh embodiment of the present disclosure further includes a rotatable turntable 5 that can be rotated relative to the airflow-guiding structure 3, and a size of the first air outlet opening 3200 can be adjusted by rotating the rotatable turntable 5 relative to the airflow-guiding structure 3. However, the aforementioned description is merely an example and is not meant to limit the scope of the present disclosure.

Beneficial Effects of the Embodiments

In conclusion, by virtue of "the airflow-guiding structure 3 including a receiving casing 30 and at least one first air outlet pipe 32 in air communication with the receiving casing 30" and "the first light-emitting module 1 (such as the UV-C radiation generating module) being received inside the airflow-guiding structure 3", when the external air F flows into the receiving casing 30 by natural convection, the external air F inside the receiving casing 30 can be sterilized by the UV-C radiation provided by the UV-C radiation generating module, and the external air F that has been sterilized by the UV-C radiation provided by the UV-C radiation generating module flows out of the receiving casing 30 through the at least one first air outlet pipe 32 by natural convection, and is then discharged out of the illumination device Z.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An illumination device, comprising:
a first light-emitting module;
a second light-emitting module adjacent to the first light-emitting module;
an airflow-guiding structure including a receiving casing for receiving the first light-emitting module, a first air inlet pipe in air communication with the receiving casing, and a first air outlet pipe in air communication with the receiving casing; and
a motion detection module disposed on the second light-emitting module or adjacent to the second light-emitting module;
wherein, when external air flows into the receiving casing through the first air inlet pipe by natural convection, the external air inside the receiving casing is sterilized by a sterilization light source provided by the first light-emitting module, and the external air that has been sterilized by the sterilization light source provided by the first light-emitting module flows out of the receiving casing through the first air outlet pipe by natural convection, and is then discharged out of the illumination device;
wherein the second light-emitting module includes a plurality of illumination assemblies, each of the illumination assemblies includes a circuit substrate and a plurality of LED chips disposed on the circuit substrate, and the motion detection module is disposed on the circuit substrate or adjacent to the circuit substrate.

2. The illumination device according to claim 1, wherein the airflow-guiding structure includes a second air outlet pipe in air communication with the receiving casing, and the external air that has been sterilized by the sterilization light source provided by the first light-emitting module flows out of the receiving casing through the second air outlet pipe by natural convection and is then discharged out of the illumination device; wherein the first air outlet pipe includes a first vertical air outlet portion in air communication with the receiving casing and a first horizontal air outlet portion in air communication with the first vertical air outlet portion, the first air outlet pipe includes a first air outlet opening, and the airflow-guiding structure includes a first air outlet filter disposed inside the first air outlet opening; wherein the second air outlet pipe includes a second vertical air outlet portion in air communication with the receiving casing and a second horizontal air outlet portion in air communication with the second vertical air outlet portion, the second air outlet pipe includes a second air outlet opening, and the airflow-guiding structure includes a second air outlet filter disposed inside the second air outlet opening; wherein the first light-emitting module is an ultraviolet-C (UV-C) radiation generating module for providing UV-C radiation having a wavelength between 100 nm and 280 nm, the second light-emitting module is an illumination generating module for generating an illumination light source, and the first light-emitting module is surrounded by the second light-emitting module or juxtaposed with the second light-emitting module.

3. The illumination device according to claim 1, wherein the first air inlet pipe includes a first left air inlet opening and a first right air inlet opening, and the airflow-guiding structure includes a first left filter disposed inside the first left air inlet opening and a first right filter disposed inside the first right air inlet opening; wherein the first air inlet pipe includes a first vertical air inlet portion in air communication with the receiving casing and a first horizontal air inlet portion in air communication with the first vertical air inlet portion, and the first left air inlet opening and the first right air inlet opening are respectively formed on two opposite lateral sides of the first horizontal air inlet portion; wherein the first air inlet pipe is disposed on a bottom side of the airflow-guiding structure, and the sterilization light source provided by the first light-emitting module is blocked by the first horizontal air inlet portion of the first air inlet pipe, so as to prevent the sterilization light source provided by the first light-emitting module from being projected onto a region under the first air inlet pipe.

4. The illumination device according to claim 1, wherein the airflow-guiding structure includes a second air inlet pipe in air communication with the receiving casing, and the external air flows into the receiving casing through the second air inlet pipe by natural convection; wherein the second air inlet pipe has a second left air inlet opening and a second right air inlet opening, and the airflow-guiding structure includes a second left filter disposed inside the second left air inlet opening and a second right filter disposed inside the second right air inlet opening; wherein the second air inlet pipe includes a second vertical air inlet portion in air communication with the receiving casing and a second horizontal air inlet portion in air communication with the second vertical air inlet portion, and the second left air inlet opening and the second right air inlet opening are respectively formed on two opposite lateral sides of the second horizontal air inlet portion; wherein the second air inlet pipe is disposed on a bottom side of the airflow-guiding structure, and a sterilization light source provided by the second light-emitting module is blocked by the second horizontal air inlet portion of the second air inlet pipe, so as to prevent the sterilization light source provided by the second light-emitting module from being projected onto a region under the second air inlet pipe; wherein the first light-emitting module is an ultraviolet-C (UV-C) radiation generating module for providing UV-C radiation having a wavelength between 100 nm and 280 nm, the second light-emitting module is an illumination generating module for generating an illumination light source, and the first light-emitting module is surrounded by the second light-emitting module or juxtaposed with the second light-emitting module.

5. An illumination device, comprising:
a first light-emitting module;
a second light-emitting module adjacent to the first light-emitting module;
an airflow-guiding structure including a receiving casing, a first air inlet pipe in air communication with the receiving casing, and a first air outlet pipe in air communication with the receiving casing, wherein the first light-emitting module is received inside the airflow-guiding structure; and
a motion detection module disposed on the second light-emitting module or adjacent to the second light-emitting module;

wherein the second light-emitting module includes a plurality of illumination assemblies, each of the illumination assemblies includes a circuit substrate and a plurality of LED chips disposed on the circuit substrate, and the motion detection module is disposed on the circuit substrate or adjacent to the circuit substrate.

6. The illumination device according to claim 5, wherein the airflow-guiding structure includes a second air outlet pipe in air communication with the receiving casing, and the external air that has been sterilized by a sterilization light source provided by the first light-emitting module flows out of the receiving casing through the first air outlet pipe and the second air outlet pipe by natural convection and is then discharged out of the illumination device; wherein the first air outlet pipe includes a first vertical air outlet portion in air communication with the receiving casing and a first horizontal air outlet portion in air communication with the first vertical air outlet portion, the first air outlet pipe includes a first air outlet opening, and the airflow-guiding structure includes a first air outlet filter disposed inside the first air outlet opening; wherein the second air outlet pipe includes a second vertical air outlet portion in air communication with the receiving casing and a second horizontal air outlet portion in air communication with the second vertical air outlet portion, the second air outlet pipe includes a second air outlet opening, and the airflow-guiding structure includes a second air outlet filter disposed inside the second air outlet opening; wherein the first light-emitting module is an ultraviolet-C (UV-C) radiation generating module for providing UV-C radiation having a wavelength between 100 nm and 280 nm, the second light-emitting module is an illumination generating module for generating an illumination light source, and the first light-emitting module is surrounded by the second light-emitting module or juxtaposed with the second light-emitting module.

7. The illumination device according to claim 5, wherein the first air inlet pipe includes a first left air inlet opening and a first right air inlet opening, and the airflow-guiding structure includes a first left filter disposed inside the first left air inlet opening and a first right filter disposed inside the first right air inlet opening; wherein the first air inlet pipe includes a first vertical air inlet portion in air communication with the receiving casing and a first horizontal air inlet portion in air communication with the first vertical air inlet portion, and the first left air inlet opening and the first right air inlet opening are respectively formed on two opposite lateral sides of the first horizontal air inlet portion; wherein the first air inlet pipe is disposed on a bottom side of the airflow-guiding structure, and a sterilization light source provided by the first light-emitting module is blocked by the first horizontal air inlet portion of the first air inlet pipe, so as to prevent the sterilization light source provided by the first light-emitting module from being projected onto a region under the first air inlet pipe.

8. The illumination device according to claim 5, wherein the airflow-guiding structure includes a second air inlet pipe in air communication with the receiving casing, and the external air flows into the receiving casing through the first air inlet pipe and the second air inlet pipe by natural convection; wherein the second air inlet pipe has a second left air inlet opening and a second right air inlet opening, and the airflow-guiding structure includes a second left filter disposed inside the second left air inlet opening and a second right filter disposed inside the second right air inlet opening; wherein the second air inlet pipe includes a second vertical air inlet portion in air communication with the receiving casing and a second horizontal air inlet portion in air communication with the second vertical air inlet portion, and the second left air inlet opening and the second right air inlet opening are respectively formed on two opposite lateral sides of the second horizontal air inlet portion; wherein the second air inlet pipe is disposed on a bottom side of the airflow-guiding structure, and a sterilization light source provided by the second light-emitting module is blocked by the second horizontal air inlet portion of the second air inlet pipe, so as to prevent the sterilization light source provided by the second light-emitting module from being projected onto a region under the second air inlet pipe; wherein the first light-emitting module is an ultraviolet-C (UV-C) radiation generating module for providing UV-C radiation having a wavelength between 100 nm and 280 nm, the second light-emitting module is an illumination generating module for generating an illumination light source, and the first light-emitting module is surrounded by the second light-emitting module or juxtaposed with the second light-emitting module.

9. An illumination device, comprising:
an ultraviolet-C (UV-C) radiation generating module for providing UV-C radiation having a wavelength between 100 nm and 280 nm;
an illumination generating module adjacent to the UV-C radiation generating module;
an airflow-guiding structure including a receiving casing for receiving the UV-C radiation generating module and at least one first air outlet opening in air communication with the receiving casing; and
a motion detection module disposed on the illumination generating module or adjacent to the illumination generating module;
wherein, when external air flows into the receiving casing by natural convection, the external air inside the receiving casing is sterilized by the UV-C radiation provided by the UV-C radiation generating module, and the external air that has been sterilized by the UV-C radiation provided by the UV-C radiation generating module flows out of the receiving casing through the at least one first air outlet opening by natural convection, and is then discharged out of the illumination device;
wherein the UV-C radiation generating module is a first light-emitting module, and the illumination generating module is a second light-emitting module; wherein the second light-emitting module includes a plurality of illumination assemblies, each of the illumination assemblies includes a circuit substrate and a plurality of LED chips disposed on the circuit substrate, and the motion detection module is disposed on the circuit substrate or adjacent to the circuit substrate.

\* \* \* \* \*